United States Patent [19]

Das et al.

[11] Patent Number: 4,474,972
[45] Date of Patent: Oct. 2, 1984

[54] 7-OXABICYCLOHEPTANE PROSTAGLANDIN INTERMEDIATES AND METHOD FOR PREPARING SAME

[75] Inventors: Jagabandhu Das, Plainsboro; Martin F. Haslanger, Lambertville, both of N.J.

[73] Assignee: E. R. Squibb & Sons, Inc., Princeton, N.J.

[21] Appl. No.: 474,761

[22] Filed: Mar. 14, 1983

[51] Int. Cl.$^3$ .......................................... C07D 307/00
[52] U.S. Cl. ................................................. 549/463
[58] Field of Search ....................................... 549/463

[56] References Cited
U.S. PATENT DOCUMENTS
4,143,054 3/1979 Sprague ............................ 549/463

Primary Examiner—Henry R. Jiles
Assistant Examiner—Bernard Dentz
Attorney, Agent, or Firm—Lawrence S. Levinson; Burton Rodney

[57] ABSTRACT

Optically active 7-oxabicycloheptane prostaglandin intermediates are provided having the general structure

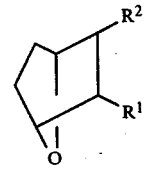

wherein one of $R^1$ and $R^2$ is —COOH,

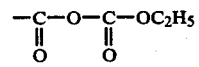

or —CH$_2$OH and the other is

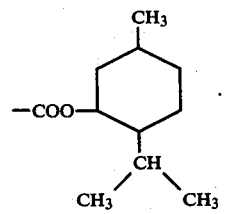

A method for preparing the above intermediates is also provided.

10 Claims, No Drawings

7-OXABICYCLOHEPTANE PROSTAGLANDIN INTERMEDIATES AND METHOD FOR PREPARING SAME

FIELD OF THE INVENTION

The present invention relates to optically active intermediates for use in preparing 7-oxabicycloheptane prostaglandin analogs and to a method for preparing such intermediates.

BACKGROUND OF THE INVENTION

U.S. Pat. No. 4,143,054 to Sprague dated Mar. 6, 1979 discloses 7-oxabicycloheptane and 7-oxabicycloheptene prostaglandin analogs which are prepared by the following methods.

In a first method maleic anhydride is made to react with an unsubstituted or substituted furan of the formula

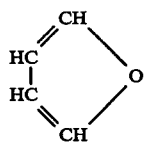

to form a compound of the formula

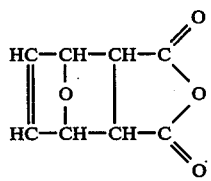

which is reduced to form

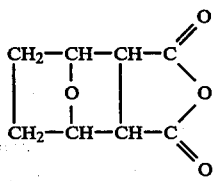

The above compound is then further reduced to form

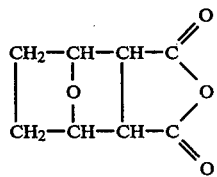   A

Treatment of the above compound with diisobutylaluminum hydride or diisobutylborane yields

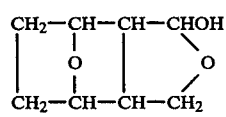   B

Submitting compound B to Wittig reaction conditions produces

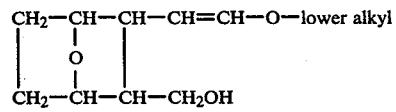   C

Compound C is then acylated and then hydrolyzed to form the aldehyde

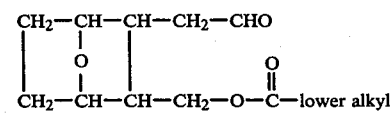   D

All of the above compounds are in the form of racemic mixtures.

Aldehyde D is subjected to a Wittig reaction to form a compound of the structure

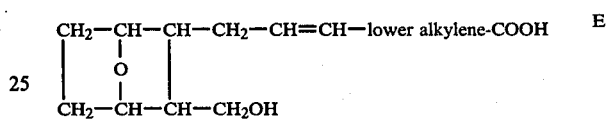   E which is esterified to form the corresponding lower alkyl ester. The hydroxymethyl group in the 3-position of the ester is then oxidized to obtain the aldehyde

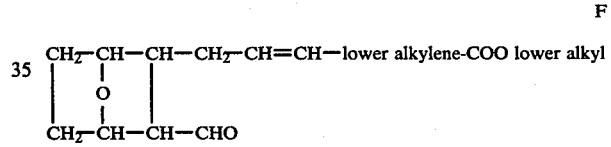   F

Aldehyde F which is in the form of a racemic mixture is employed to form 7-oxabicycloheptane prostaglandin analogs.

BRIEF DESCRIPTION OF THE INVENTION

In accordance with the present invention, a method is provided for forming the aldehyde F also depicted graphically as

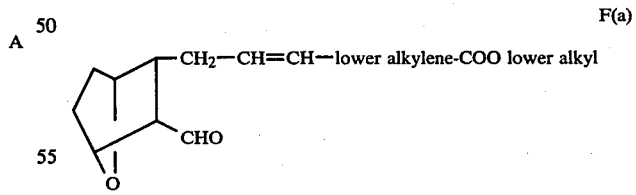   F(a)

in the form of its optically active isomer as opposed to a racemic mixture of two enantiomers as disclosed by Sprague in U.S. Pat. No. 4,143,054. The optically active aldehyde F(a) is then employed to form optically active 7-oxabicycloheptane prostaglandin analogs, for example, using the technique described by Sprague in U.S. Pat. No. 4,143,054.

In carrying out the method of the invention as described hereinafter several novel optically active intermediates are formed having the following formula

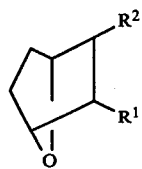

wherein one of R¹ and R² is —COOH,

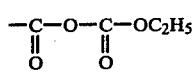

or —CH₂OH and the other is

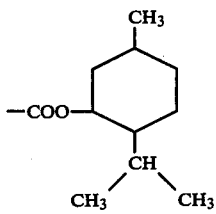

and includes the following compounds:

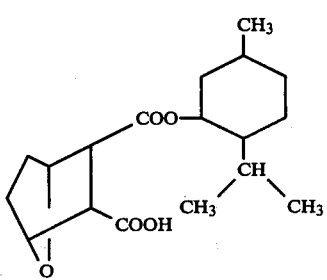

(1S,2R,3S,4R)cis-exo 2-1-Menthoxycarbonyl-
3-carboxyl-7-oxabicyclo[2.2.1]heptane

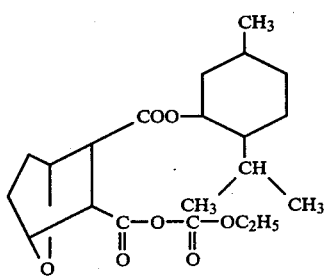

(1S,2R,3S,4R)cis-exo 2-1-Menthoxycarbonyl-
3-ethoxycarbonyloxycarbonyl-7-oxabicyclo[2.2.1]heptane

II

III

-continued

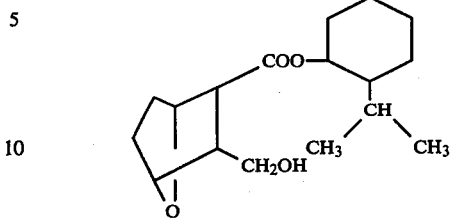

(1S,2R,3S,4R) cis-exo 2-1-Menthoxycarbonyl-3-
hydroxymethyl-7-oxabicyclo[2.2.1]heptane

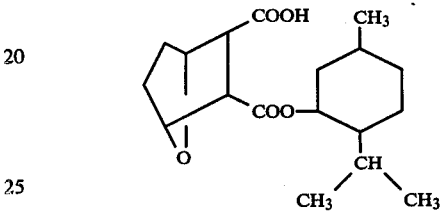

(1R,2S,3R,4S) cis-exo 2-d-Menthoxycarbonyl-3-
carboxyl-7-oxabicyclo[2.2.1]heptane

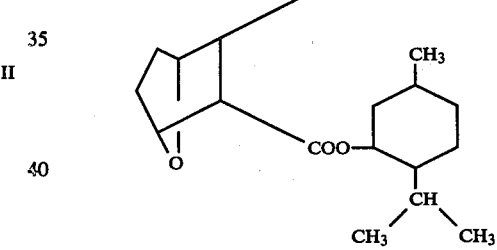

(1R,2S,3R,4S) cis-exo 2-d-Menthoxycarbonyl-3-
ethoxycarbonyloxycarbonyl-7-oxabicyclo[2.2.1]heptane

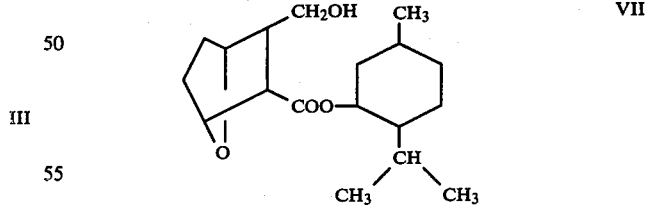

(1R,2S,3R,4S) cis-exo 2-d-Menthoxycarbonyl-3-
hydroxymethyl-7-oxabicyclo[2.2.1]heptane

IV

V

VI

VII

The method of the present invention for forming optically active or chiral intermediates for use in preparing optically active 7-oxabicycloheptane prostaglandin analogs may be summarized in the following reaction sequence.

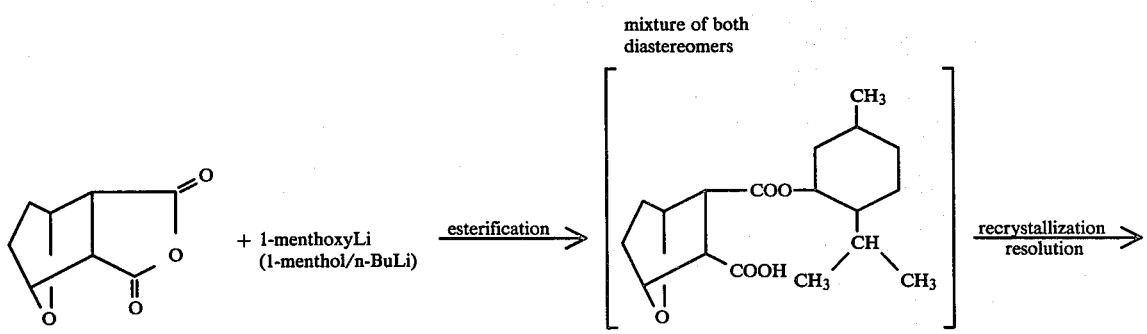
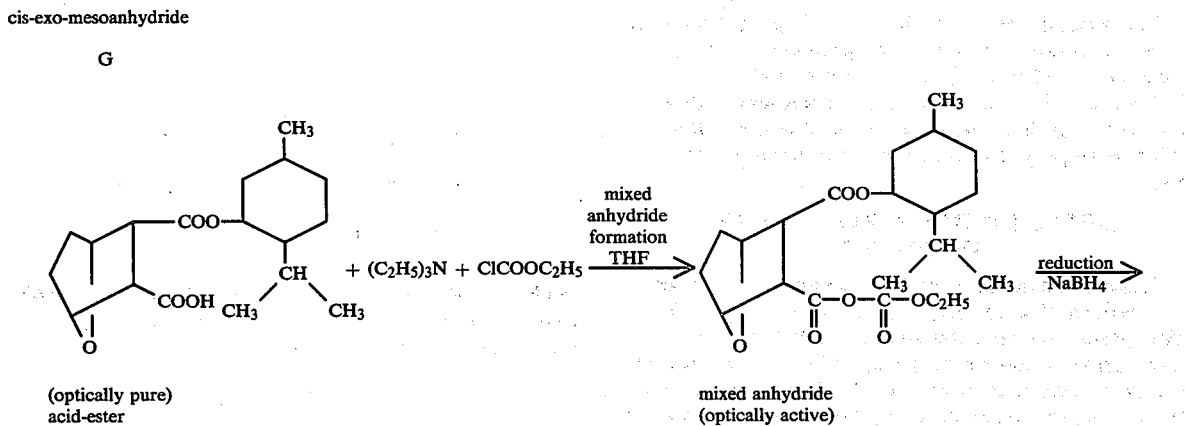
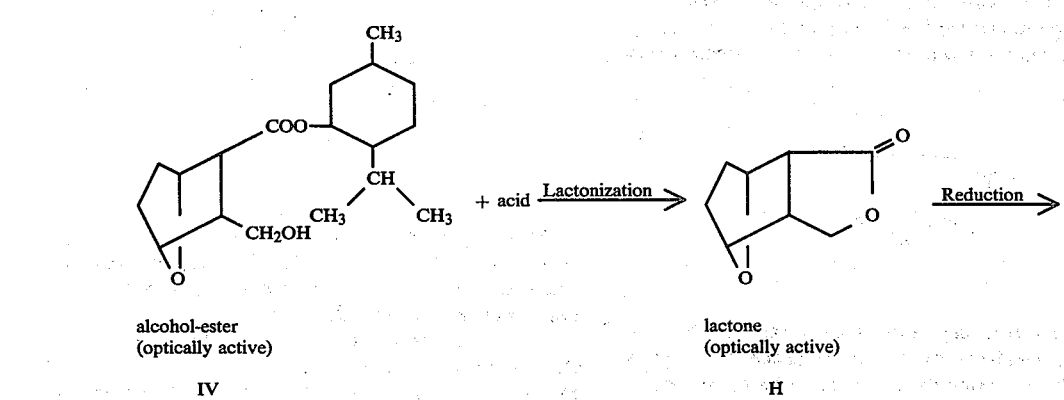
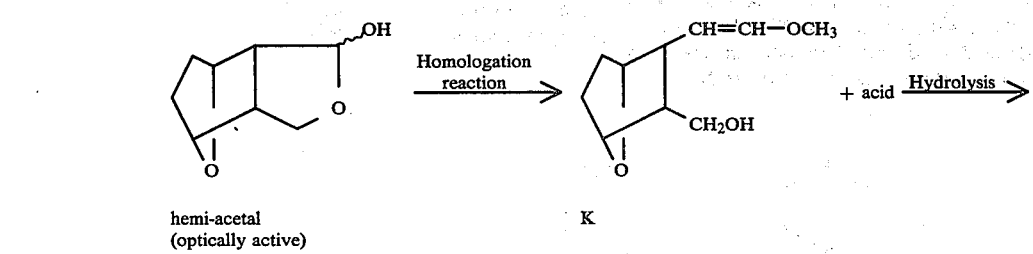
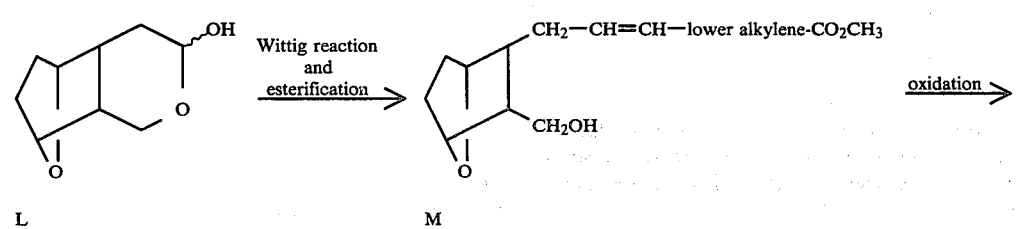

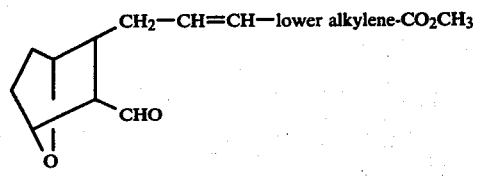

N

The reaction sequence for preparing the optically active antipodes or mirror images of compounds of formulae II, III and IV, namely compounds of formulae V, VI and VII, respectively, may be prepared following the above reaction sequence except that d-menthoxylithium is employed in place of the corresponding l-isomer.

DETAILED DESCRIPTION OF THE INVENTION

The method of the invention is an advance over prior art methods for forming optically active 7-oxabicycloheptane prostaglandin analogs in that the resolution is performed at a very early stage of the synthesis, preferably on a meso-intermediate. In the present method, the undesired diasteromer can be reconverted to the meso-adduct and recycled. Thus, in principle, the meso-intermediate is transformed to a single diastereomer.

In carrying out the method of the invention, referring to the above reaction sequence, the cis-exo-mesoanhydride G

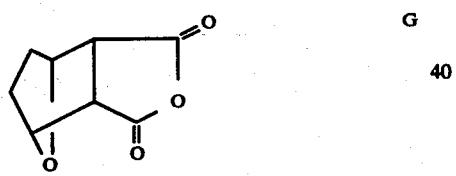

G is esterified by reacting same with l-menthoxylithium (l-menthol/n-butyllithium) in the presence of an inert solvent such as tetrahydrofuran at reduced temperatures of below about 78° C., to form a mixture of diastereomers of formula II which is recrystallized, for example, from methylene chloride-ethyl acetate and resolved to form the optically active acid-ester isomer II

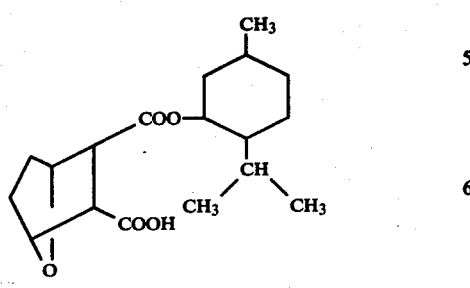

The acid-ester II is allowed to react with triethylamine and ethylchloroformate in an inert solvent such as tetrahydrofuran to form the optically active mixed anhydride III

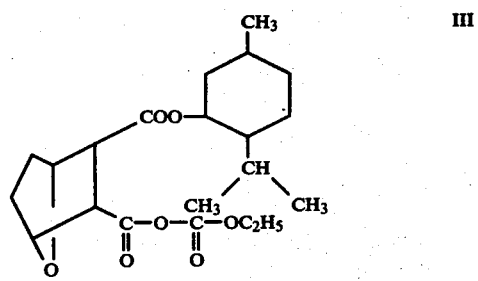

III which is then reduced, for example, by reaction with sodium borohydride in alcohol solvent to form the optically active alcohol-ester IV

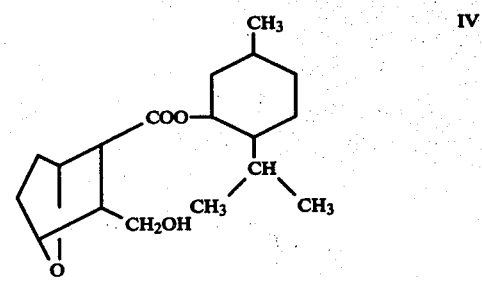

IV

As indicated, replacement of the l-menthoxy Li compound with the corresponding d-isomer, in the reaction sequence produces the corresponding optically active antipodes V, VI and VII.

The alcohol ester IV or VII of the invention may then be employed to form optically active lactone H or H' by subjecting alcohol ester IV or VII, respectively, to a lactonization reaction, for example, reacting with hydrochloric acid in methylene chloride.

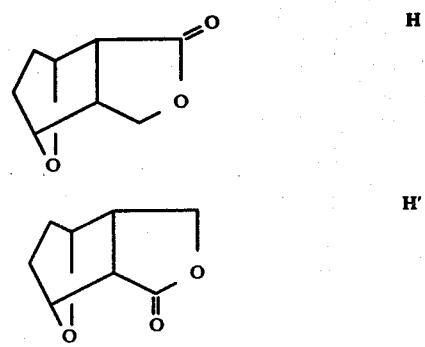

Thus, it is seen that lactone H or H' can be obtained from the meso-anhydride G without recourse to any chromatographic purification.

The lactone H or H' may now be employed to form the prostaglandin aldehyde analog starting material N or N'

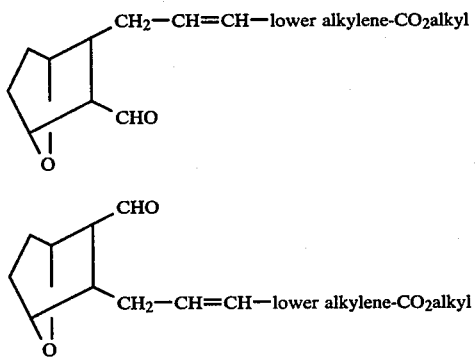

following the above reaction sequences and as described in U.S. Pat. No. 4,143,054 to Sprague.

The prostaglandin aldehyde analog N or N' may then be employed to prepare 7-oxabicycloheptane prostaglandins following the procedure as set out in U.S. Pat. No. 4,143,054 to Sprague. Such prostaglandins derivatives are useful in the treatment of thrombolytic disease as explained in the above Sprague patent.

The following Examples represent preferred embodiments of the present invention.

EXAMPLE 1

(1S,2R,3S,4R) cis-exo 2-l-Menthoxycarbonyl-3-carbonyl-7-oxabicyclo[2.2.1]heptane To a solution of 10.3 g of l-menthol (66 mmole) in 40 ml of dry THF was added dropwise at 0° C., 37.5 ml of a 1.6M solution of n-butyllithium in hexane (60 mmole). After stirrring for 1 hour, the solution of l-menthoxylithium was added via a canula to a solution of 10 g of cis-exo 7-oxabicyclo[2.2.1]heptane-2,3-dicarboxylic anhydride (mesoanhydride) (60 mmole) in 120 ml of THF at −78° C. under a positive argon pressure. The reaction mixture was stirred at −78° C. for 1 hour, whereupon it was poured into saturated sodium dihydrogen phosphate solution. Extractive work up in methylene chloride, followed by drying the organic layer over anhydrous magnesium sulfate and concentration in vacuo gave 20.2 g of white crystalline product. The residue was dissolved in 200 ml of methylene chloride-ethylacetate (1:4) and cooled at 0°-5° C. Precipitated acid-ester was filtered off, washed with cold ethylacetate and dried in vacuo to yield 5.1 g of diastereomerically pure title acid ester (26.4% yield, 53% efficiency), m.p. 179°-180° C.; $[\alpha]_D$: −63.9° (C 12.2, chloroform).

$$^{13}\text{C-NMR} \frac{(\text{CDCl}_3/\text{TMS}):}{\text{CD}_3\text{OD}}$$

δ172.86, 170.7; 78.56, 78.1, 74.8, 52.2, 52.00, 46.8, 40.0; 34.0; 31.2, 28.8, 26.0, 23.2, 21.7, 20.5, 16.0 ppm.

P.M.R. (CDCl$_3$): δ5.00 (m,1H), 4.86 (m, 1H), 4.69 (dt, 1H, J=11, 4.4 Hz), 3.00 (d, 1H, J=9.5 Hz), 2.93 (d, J=9.5 Hz, 1H).

Ms (CI), m/e 325 (M+ +1), 187, 169.

Anal. Calcd for $C_{18}H_{28}O_5$: C, 66.64; H, 8.70; Found: C, 66.51; H, 8.64.

EXAMPLE 2

(1S,2R,3S,4R) cis-exo 2-l-Menthoxycarbonyl-3-ethoxycarbonyloxycarbonyl-7-oxabicyclo[2.2.1]heptane To a solution of 1 g of Example 1 acid ester (3.09 mmole) in 10 ml of dry THF was added with stirring at 0°-5° C., 850 μl of triethylamine (6 mmole) followed by 570 μl (6 mmole) of distilled ethylchloroformate. After stirring for 1 hour, the reaction mixture was diluted with 50 ml of dry ether and filtered through anhydrous magnesium sulfate. The filtrate was concentrated in vacuo to obtain optically active title crystalline mixed anhydride.

EXAMPLE 3

(1S,2R,3S,4R) cis-exo 2-l-Menthoxycarbonyl-3-hydroxymethyl-7-oxabicyclo[2.2.1]heptane Crude Example 2 mixed anhydride (1.2 g) was dissolved in 10 ml of dry THF and 15 ml of absolute ethanol, cooled in an ice-water bath and 230 mg of solid sodium borohydride (6 mmole, 2 equiv.) was added with stirring.

After 15 minutes, the reaction mixture was poured into 50 ml of ice-cold 1N aqueous hydrochloric acid solution and extracted with methylene chloride. The methylene chloride extract was dried over anhydrous magnesium sulfate, concentrated in vacuo to obtain crude title alcohol-ester, $^{13}$C-N.M.R. (CDCl$_3$)-δ171.75, 78.5, 75.00, 62.2, 51.00, 50.24, 47.13, 40.83, 34.33, 31.48, 29.40, 29.10, 26.35, 23.49, 22.06, 20.83, 16.34 ppm.

EXAMPLE 4

[1S-(1α,2β(5Z),3β,4α)]-7-[3-Formyl-7-oxabicyclo[2.2.1]hept-2-yl]-5-heptenoic acid, methyl ester

A. (3aR,4R,7S,7aR) exo Hexahydro-4,7-epoxyisobenzofuran-1(3H)-one

Crude Example 3 alcohol-ester (about 1 g) was dissolved in 10 ml of methylene chloride and treated with 60 mg of p-toluene sulfonic acid (10 mole %). After 15 minutes, the reaction mixture was diluted with methylene chloride and washed with saturated sodium bicarbonate solution. The methylene chloride extract was dried over anhydrous magnesium sulfate and concentrated in vacuo to leave a crystalline residue. On addition of hexane, the title lactone A was precipitated. It was filtered, washed several times with hexane, dried in vacuo to obtain 430 mg of colorless crystalline title lactone (90% overall yield from the acid ester of Example 1), m.p. 68.5°-69.5° C.; $[\alpha]_D$ = +114.2°. (C 16.7, chloroform); $^{13}$C—N.M.R. (CDCl$_3$):—δ177.34, 82.26, 79.60, 72.13, 49.53, 43.23, 28.55, 27.45 ppm; MS (CI), m/e 155 (M$^+$+1); MS (EI), m/e 154 (M$^+$); Anal. Calcd for $C_8H_{10}O_3$: C, 62.32; H, 6.54; Found: C, 62.05; H, 6.56.

B. (3aR,4R,7S,7aR) exo Octahydro-4,7-epoxyisobenzofuran-1-ol

A solution of 308 mg of title A (+) lactone (2 mmole) in 5 ml of dry toluene at −78° C. was treated dropwise with 2.4 ml of a 25% by weight solution of diisobutylaluminium hydride in toluene (4 mmole, 2 equiv.). After 30 minutes at −78° C., the reaction mixture was quenched by addition of acetic acid. It was then poured into 1N aqueous hydrochloric acid solution. The aqueous layer was saturated with sodium chloride and exhaustively extracted with methylene chloride. The methylene chloride extract was dried over anhydrous magnesium sulfate and concentrated in vacuo to give 265 mg of title B hemi-acetal, m.p. 65°–67° C., $[\alpha]_D = +51.94°$ (C 10.3, methanol), $^{13}$C—N.M.R. (CDCl$_3$)—$\delta$102.39, 98.43, 81.03, 78.30, 71.29, 68.62, 56.22, 53.30, 48.88, 47.58, 28.56, 28.17, 27.26 ppm; MS (CI)—m/e 157 (M$^+$+1), 139.

C. (1R,4S) exo-3-(2-Methoxyethenyl)-7-oxabicyclo[2.2.1]heptane-

A slurry of methoxymethyltriphenylphosphonium chloride (15.2 g, 0.0443 mole) in toluene (500 ml) was treated with a solution of lithium diisopropyl amide (LDA) (prepared from 1.6M n-butyl lithium (27.6 ml, 0.0442 mole) and diisopropyl amine (7.7 ml, 0.055 mole) in pentane) in tetrahydrofuran (10 ml) at 0° C. The mixture was stirred at room temperature for thirty minutes then treated via a solid addition device with title B hemi-acetal (2 g, 0.0128 mole). The mixture was stirred at room temperature for three days then poured into brine (1000 ml), treated with 10% hydrochloric acid until pH=6.5, then extracted with ether (3×200 ml). The combined ether extracts were dried over magnesium sulfate and concentrated in vacuo. The residue was triturated with hexane/ether and filtered. The filtrate was concentrated in vacuo. The residue was chromatographed on LP-1 silica gel (300 ml) eluting with dichloromethane and ether/dichloromethane (1:1) to yield the desired product contaminated with phosphine salts. This material was distilled in vacuo to yield 1.6 g of title compound, b.p. 110° C./0.05 cm.

$[\alpha]_D = -54°$ $[\alpha]_{365}^{Hg} = -168°$, C=11 mg/ml CHCl$_3$.
TLC: silica gel; ethyl acetate/dichloromethane (1:1); $R_f=0.2$; vanillin spray and heat.

D. (5S,8R) exo Octahydro-5,8-epoxy-1H-benzopyran-3-ol

A solution of title C compound (1.6 g, 0.0087 mole) in 20% trifluoroacetic acid/water (16 ml) was stirred at room temperature under nitrogen for two hours. The solution was made basic with solid sodium bicarbonate. The aqueous mixture was then saturated with sodium chloride and extracted with chloroform (10×50 ml). The combined extracts were concentrated in vacuo. The resultant oil contained significant amounts of partial hydrolysis products. This material was subjected to a second treatment with TFA/water as above and after a second workup as above yielded a solid product which was chromatographed on LP-1 silica gel (150 ml) eluting with ether/dichloromethane (1:9) and ether to yield 1.3 g of title D compound, m.p. 94°–96° C.

TLC: silica gel; ethyl acetate/dichloromethane (1:1); $R_f=0.1$; vanillin spray and heat. $[\alpha]_D = -26.8°$, C=10 mg/ml MeOH.

E. [1S-(1α,2β(5Z),3β,4α)]-7-[3-Hydroxymethyl-7-oxabicyclo[2.2.1]hept-2-yl]-5-heptenoic acid and

F. [1S-(1α,2β(5Z),3β,4α)]-7-Hydroxymethyl-7-oxabicyclo[2.2.1]hept-2-yl]-5-heptenoic acid, methyl ester A slurry of 4-carboxybutyltriphenylphosphonium bromide (10.18 g, 0.023 mole) in anhydrous dimethylsulfoxide (20 ml) was treated with a solution of freshly prepared dimsyl ion at 15° C. until an orange coloration persisted. A second equivalent of dimsyl ion was added to form the desired ylide. The deep red mixture was stirred at room temperature for 30 minutes then treated with title D compound (1.3 g, 0.0076 mole) dissolved in 10 ml of anhydrous dimethylsulfoxide. The reaction mixture was stirred at room temperature for 2 hours then quenched with a solution of glacial acetic acid (1.4 g, 0.023 mole) in ether (10 ml). The mixture was poured into brine (1000 ml), acidified to pH=2 with concentrated hydrochloric acid and extracted with ethyl acetate (6×50 ml). The combined extracts were concentrated in vacuo. The residue was dissolved in 5% sodium bicarbonate (150 ml) and extracted with benzene (2×100 ml) and ethyl acetate (2×100 ml). The aqueous layer was acidified to pH=2 with concentrated hydrochloric acid and extracted with ethyl acetate (5×50 ml). The combined ethyl acetate extracts were dried over magnesium sulfate and concentrated in vacuo. The residue was dissolved in ether (100 ml) and chilled overnight. The precipitated phosphine salts were removed by filtration. The filtrate was concentrated in vacuo to yield 2.1 g of product which contained title E compound contaminated with small amounts of phosphine salts. Title E compound was dissolved in 100 ml of ether, treated with excess ethereal diazomethane solution and stirred at room temperature for 1 hour. The reaction mixture was quenched with glacial acetic acid/ether solution, washed with 5% sodium bicarbonate, then concentrated in vacuo. The residue was chromatographed on LP-1 silica gel (400 ml) eluting with ether/hexane (1:1) and ether to yield 1.4 g of title F compound.

TLC of E: silica gel; ether; $R_f=0.2$; vanillin spray and heat.
TLC of F: silica gel; ether; $R_f=0.4$; vanillin spray and heat.
$[\alpha]_D$ of F = $-12.3°$, C=27 mg/ml (MeOH).

G. [1S-(1α,2β(5Z),3β,4α)]-7-[3-Formyl-7-oxabicyclo[2.2.1]hept-2-yl]-5-heptenoic acid, methyl ester A solution of pyridine (5.02 ml, 0.062 mole) in anhydrous dichloromethane (175 ml) was treated portionwise with chromium trioxide (3.12 g, 0.0312 mole) then stirred vigorously at room temperature for 30 minutes. The red solution was then treated with dry celite (10 g) followed by title F compound (1.4 g, 0.0052 mole) dissolved in dichloromethane (10 ml). The mixture was stirred at room temperature for 30 minutes then filtered through celite. The filtrate was washed with 5% sodium bicarbonate (2×100 ml), 10% hydrochloric acid (2×100 ml), 5% sodium bicarbonate (1×100 ml), dried over magnesium sulfate and concentrated in vacuo. The residue was dissolved in ether, treated with carbon and filtered. The filtrate was concentrated in vacuo to yield 1.3 g of title aldehyde, one spot by TLC.

TLC: silica gel; hexane/ether (1:1); $R_f=0.5$; vanillin spray and heat.

EXAMPLE 5

(1R,2S,3R,4S) cis-exo 2-d-Menthoxycarbonyl-3-carboxyl-7-oxabicyclo[2.2.1]heptane A solution of 16 g of d-menthol (102 mmole) in 60 ml of dry THF was treated dropwise with 62.5 ml of a 1.6M solution of n-butyllithium in hexane at 0° C. After 1 hour at 0° C., the solution of d-menthoxylithium was added via a canula to a solution of 16.8 g of cis-exo 7-oxabicyclo[2.2.1]heptane-2,3-dicarboxylic anhydride (mesoanhydride) (100 mmole) in 200 ml of dry THF at −78° C. Stirring was continued for additional 1 hour, whereupon the reaction mixture was poured into aqueous sodium dihydrogen phosphate solution. Extractive work up in methylene chloride, followed by drying of the organic extract over anhydrous magnesium sulfate and concentration in vacuo gave a white crystalline residue, which was dissolved in 300 ml of methylene chloride ethyl acetate (1:4) and cooled at 0°–5° C. Crystallized acid-ester was filtered, washed with cold ethyl acetate and dried in vacuo to obtain 10.3 g of diastereomerically pure title compound in 31.8% yield (64% chiral efficiency), m.p. 176°–178° C., $[\alpha]_D = +64.3°$ (C 13.1, chloroform). MS (CI), m/e 325 (M$^+$+1), $^{13}$C—N.M.R. and 400 MHz P.M.R. spectra identical as those of compound of Example 1.

Anal. Calcd for $C_{18}H_{28}O_5$: C, 66.64; H, 8.70; Found: C, 66.64; H, 8.71.

EXAMPLE 6

(1R,2S,3R,4S) cis-exo 2-d-Menthoxycarbonyl-3-ethoxycarbonyloxycarbonyl-7-oxabicyclo[2.2.1]heptane To a solution of 1 g of Example 5 acid ester (3.09 mmole) in 10 ml of dry THF was added with stirring at 0°–5° C., 850 μl of triethylamine (6 mmole) followed by 570 μl (6 mmole) of distilled ethylchloroformate. After stirring for 1 hour, the reaction mixture was diluted with 50 ml of dry ether and filtered through anhydrous magnesium sulfate. The filtrate was concentrated in vacuo to obtain optically active title crystalline mixed anhydride.

EXAMPLE 7

(1R,2S,3R,4S) cis-exo 2-d-Menthoxycarbonyl-3-hydroxymethyl-7-oxabicyclo[2.2.1]heptane Crude Example 6 mixed anhydride (1.2 g) was dissolved in 10 ml of dry THF and 15 ml of absolute ethanol, cooled in an ice-water bath and 230 mg of solid sodium borohydride (6 mmole, 2 equivalents) was added with stirring.

After 15 minutes, the reaction mixture was poured into 50 ml of ice-cold 1N aqueous hydrochloric acid solution and extracted with methylene chloride. The methylene chloride extract was dried over anhydrous magnesium sulfate, concentrated in vacuo to obtain crude title alcohol-ester.

EXAMPLE 8

(3aS,4S,7R,7aS) exo Hexahydro-4,7-epoxyisobenzofuran-1(3H)-one

Crude Example 7 alcohol ester (about 1 g) was dissolved in 10 ml of methylene chloride and treated with 60 mg of p-toluene sulfonic acid (10 mole %). After 15 minutes, the reaction mixture was diluted with methylene chloride and washed with saturated sodium bicarbonate solution. The methylene chloride extract was dried over anhydrous magnesium sulfate and concentrated in vacuo to leave a crystalline residue. On addition of hexane, the title lactone was precipitated. It was filtered, washed several times with hexane, dried in vacuo to obtain 430 mg of colorless crystalline title lactone (90% overall yield from Example 5 acid ester), m.p. 67.5°–68.5° C.; $[\alpha]_D = +112.3°$ (c 11.6, chloroform); $^{13}$C—N.M.R. (CDCl$_3$)−δ177.34, 82.26, 79.60, 72.13, 49.53, 43.23, 28.55, 27.45 ppm; MS (CI), m/e 155 (M$^+$+1); MS (EI), m/e 154 (M$^+$); Anal. Calcd for $C_8H_{10}O_3$: C, 62.32; H, 6.54; Found: C, 62.10; H, 6.52.

What is claimed is:

1. A compound having the structure

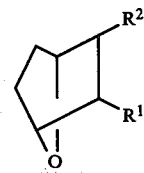

wherein one of R$^1$ and R$^2$ is —COOH,

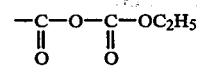

or —CH$_2$OH and the other is

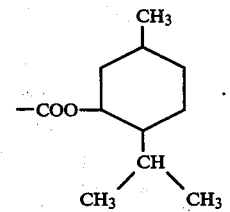

2. The compound as defined in claim 1 wherein R$^1$ is —COOH,

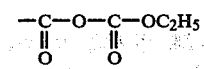

or —CH$_2$OH and R$^2$ is

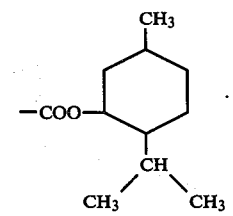

3. The compound as defined in claim 1 wherein R$^2$ is —COOH,

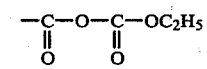

or —CH$_2$OH and R$^1$ is

4. The compound as defined in claim 1 having the formula

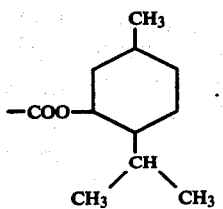

and the name (1S,2R,3S,4R) cis-exo 2-l-menthoxycarbonyl-3-carboxyl-7-oxabicyclo[2.2.1]heptane.

5. The compound as defined in claim 1 having the formula

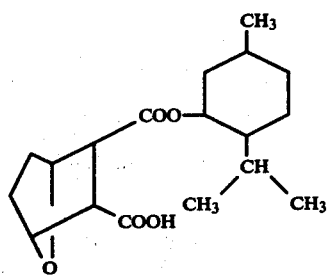

and the name (1S,2R,3S,4R) cis-exo 2-l-menthoxycarbonyl-3-ethoxycarbonyloxycarbonyl-7-oxabicyclo[2.2.1]heptane.

6. The compound as defined in claim 1 having the formula

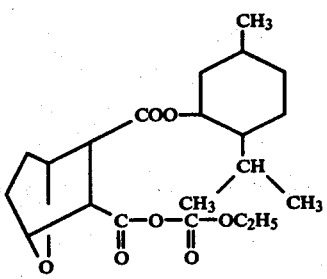

and the name (1S,2R,3S,4R) cis-exo 2-l-menthoxycarbonyl-3-hydroxymethyl-7-oxabicyclo[2.2.1]heptane.

7. The compound as defined in claim 1 having the formula

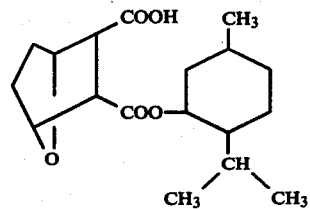

and the name (1R,2S,3R,4S) cis-exo 2-d-menthoxycarbonyl-3-carboxyl-7-oxabicyclo[2.2.1]heptane.

8. The compound as defined in claim 1 having the formula

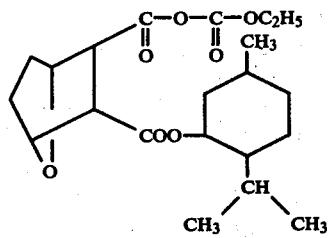

and the name (1R,2S,3R,4S) cis-exo 2-d-menthoxycarbonyl-3-ethoxycarbonyloxycarbonyl-7-oxabicyclo[2.2.1]heptane.

9. The compound as defined in claim 1 having the formula

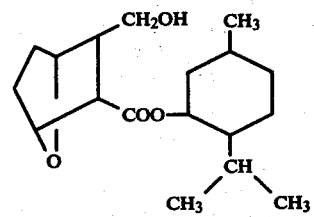

and the name (1R,2S,3R,4S) cis-exo 2-d-menthoxycarbonyl-3-hydroxymethyl-7-oxabicyclo[2.2.1]heptane.

10. A method for preparing compounds as defined in claim 1 which comprises esterifying a cis-exo-mesoanhydride of the formula

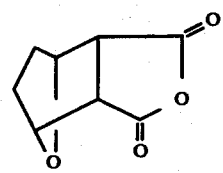

by reacting same with d or l-menthol/n-butyllithium to form a mixture of diastereomers, resolving the above mixture to recover optically active acid-ester diastereomer

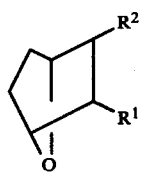

wherein $R^2$ is

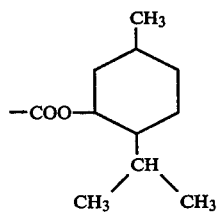

and $R^1$ is COOH where the l-menthol isomer is used and $R^2$ is COOH and $R^1$ is

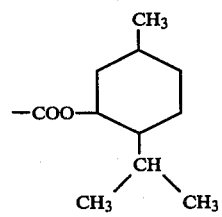

where the d-menthol isomer is used, reacting the above acid-ester with triethanolamine and ethylchloroformate to form the optically active mixed anhydride

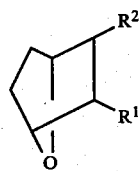

where $R^2$ is

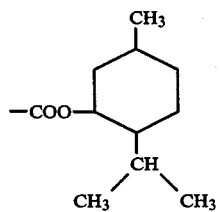

and $R^1$ is

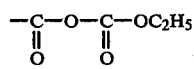

where the l-menthol isomer was is as a starting material and $R^2$ is

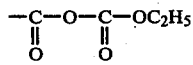

and $R^1$ is

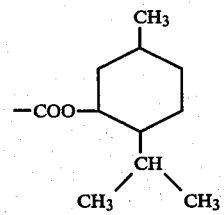

where the d-menthol isomer is used as a starting material, and reducing the above mixed anhydride to form the optically active alcohol ester

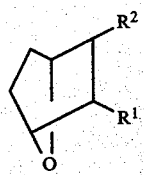

wherein $R^2$ is

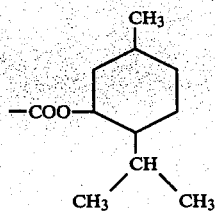

and $R^1$ is —$CH_2OH$ wherein the l-menthol isomer is used as a starting material and $R^2$ is —$CH_2OH$ and $R^1$ is

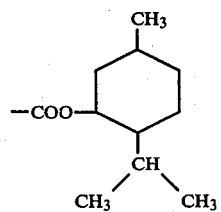

wherein the d-menthol isomer is used as a starting material.

* * * * *